(12) United States Patent
Rippl et al.

(10) Patent No.: US 8,622,681 B2
(45) Date of Patent: Jan. 7, 2014

(54) SPECIMEN CARRIER SUPPLY AND DELIVERY DEVICE

(71) Applicant: Maerzhaeuser Wetzlar GmbH & Co. KG, Wetzlar (DE)

(72) Inventors: Christopher Mark Rippl, Wetzlar (DE); Uwe Wagner, Mengerskirchen (DE); Lukas Nagel, Glessen (DE); Ralf Tide, Oberursel (DE); Sebastian Scherer, Wetzlar (DE); Andreas Loehr, Mengerskirchen (DE)

(73) Assignee: Maerzhaeuser Wetzlar GmbH & Co. KG, Wezlar (DE)

( * ) Notice: Subject to any disclaimer, the term of this patent is extended or adjusted under 35 U.S.C. 154(b) by 0 days.

(21) Appl. No.: 13/859,390

(22) Filed: Apr. 9, 2013

(65) Prior Publication Data

US 2013/0264299 A1    Oct. 10, 2013

(30) Foreign Application Priority Data

Apr. 10, 2012   (DE) .......................... 10 2012 007 134

(51) Int. Cl.
*B65H 1/00*           (2006.01)

(52) U.S. Cl.
USPC ................ 414/225.01; 414/331.03; 211/41.1; 422/63

(58) Field of Classification Search
USPC .................. 414/225.01, 222.01, 806, 331.01, 414/331.03; 211/1.51, 1.57, 41.1; 250/440.11; 422/63
See application file for complete search history.

(56) References Cited

U.S. PATENT DOCUMENTS 4,981,409 A * 1/1991 Hirose et al. ............. 414/223.01
5,622,470 A * 4/1997 Schaefer et al. ............. 414/807

(Continued)

FOREIGN PATENT DOCUMENTS

DE      1 903 380 A    7/1970
DE     94 16 199 U1    1/1995

(Continued)

OTHER PUBLICATIONS

German Office Action with English translation dated Jan. 9, 2013 (six (6) pages).

*Primary Examiner* — Korie H Chan
(74) *Attorney, Agent, or Firm* — Crowell & Moring LLP

(57) ABSTRACT

Provided is a specimen carrier supply and delivery device having at least one specimen carrier magazine with separate compartments for receiving interchangeably specimen carriers and a magazine lift, which is adjustable in height in a magazine carrier frame for receiving interchangeably specimen carrier magazines. Two pairs of bars, which stand vertically and parallel to one another, are arranged in the magazine carrier frame, wherein the magazine lift is guided in a height adjustable manner on the two complementary first bars of the bar pairs. An equal-sided coupling frame, which is aligned vertically to the plane formed by the first bars, with a bridge, which is arranged parallel to the plane, is mounted in a sliding manner on the two complementary second bars of the pairs of bars. A linear scale, which is aligned parallel to the direction of the bars, is fastened to the magazine lift. A sensor for reading the position of the coupling frame relative to the linear scale is disposed on the sliding mounting of the coupling frame. A carrier element, which is aligned transversely to the direction of the bars and is configured for a linear motor with a spindle for adjusting the height of the magazine lift relative to the current position of the sensor, is arranged on the magazine carrier frame.

6 Claims, 2 Drawing Sheets

(56) References Cited

U.S. PATENT DOCUMENTS 5,692,867 A * 12/1997 Kondo et al. ................ 414/268
6,568,770 B2 * 5/2003 Gonska et al. ............... 312/9.12
6,761,522 B2 * 7/2004 Jager ........................ 414/222.01

FOREIGN PATENT DOCUMENTS

DE  10 2005 009 756 A1  9/2006
DE  10 2008 037 876 A1  3/2010

* cited by examiner

SPECIMEN CARRIER SUPPLY AND DELIVERY DEVICE

CROSS REFERENCE TO RELATED APPLICATION

This application claims priority under 35 U.S.C. §119 from German Patent Application No. 10 2012 007 134.5, filed Apr. 10, 2012, the entire disclosure of which is herein expressly incorporated by reference.

BACKGROUND AND SUMMARY OF THE INVENTION

The invention relates to a specimen carrier supply and delivery device having at least one specimen carrier magazine with separate compartments for receiving interchangeably specimen carriers and a magazine lift, which is adjustable in height in a magazine carrier frame for receiving interchangeably specimen carrier magazines.

Devices of this type are known in different designs. They serve to provide prepared specimen carriers of various types, in particular, for an automatic analysis in a microscope. The microscope and the device with the specimen carriers are generally separate units that have to be carefully aligned with one another, in order to guarantee a reliable transfer of the specimen carriers from one unit to the other and back again. Just a slight misalignment while an automatic analysis is running may lead to an interruption in the examination process and, thus, to time delays in the entire course of the process. Maintaining a reliable transfer position becomes very difficult with microscopes that have a vertical stage adjustment for focusing the objectives on the specimen (object) plane. However, even with microscopes that have stationary microscope stages, such as inverted microscopes, problems may arise in the course of connecting to stages of fixed different heights as well as with respect to the jolts and vibrations that may occur at the place where the two units are set up, so that the two units may shift with respect to each other.

Therefore, an object of the present invention is to provide a universally usable specimen carrier supply and delivery device, which can be connected to different microscope systems and can automatically compensate for the mutual changes in height between the delivery plane and the removal plane from an initial adjustment.

Exemplary embodiments of the invention achieve this engineering object with a specimen carrier supply and delivery device having at least one specimen carrier magazine with separate compartments for receiving interchangeably specimen carriers and a magazine lift, which is adjustable in height in a magazine carrier frame for receiving interchangeably specimen carrier magazines. Two pairs of bars, which stand vertically and parallel to one another, are arranged in the magazine carrier frame, wherein the magazine lift is guided in a height adjustable manner on the two complementary first bars of the bar pairs. An equal-sided coupling frame, which is aligned vertically to the plane formed by the first bars, with a bridge, which is arranged parallel to the plane, is mounted in a sliding manner on the two complementary second bars of the pairs of bars. A linear scale, which is aligned parallel to the direction of the bars, is fastened to the magazine lift. A sensor for reading the position of the coupling frame relative to the linear scale is disposed on the sliding mounting of the coupling frame. A carrier element, which is aligned transversely to the direction of the bars and is configured for a linear motor with a spindle for adjusting the height of the magazine lift relative to the current position of the sensor, is arranged on the magazine carrier frame.

Two planes that are essential for operating the device can be moved parallel to each other at the vertical pairs of bars that are arranged in the magazine carrier frame. These planes are the plane of the specimen carriers in the compartments of the specimen carrier magazines and the plane, formed by the right-angled coupling frame, which is mounted in a sliding manner and has a bridge. The bridge is provided to be fastened to a microscope stage, so that the coupling frame with the bridge forms a reference plane that is fixed with respect to the plane of the microscope stage. The sliding mounting of the coupling frame guarantees an effortless coupling to different and also changing planes of the microscope stage. The vertical bars can be constructed in different ways for the linear guidance. The compartments in the specimen carrier magazines can be adapted to various forms of specimen carriers, such as rectangular specimen slides with a glass cover, Petri dishes, or titer plates. Due to the equal-sided configuration of the coupling frame the specimen carrier magazines can always be moved up and down equidistant to the lateral boundary of the microscope stage when coupling a microscope stage to the bridge.

Their relative position to each other can be determined with the aid of the linear scale, which is fastened to the magazine lift, and the sensor, which is arranged on the coupling frame that is mounted in a sliding manner. In order to transfer the specimen carriers from the specimen carrier magazine to the microscope stage, the respective height adjustment of the coupling frame forms the reference plane. The magazine lift can be moved relative to the reference position of the coupling frame by means of the linear motor, fastened to the magazine carrier frame, and the spindle, which is moved thereby. Therefore, when the distance between the compartments in the specimen carrier magazine is known, it is possible to make available for removal each desired specimen carrier in the transfer plane, determined during an initial adjustment, relative to the reference plane.

The sensor, which is fastened to the coupling frame, is mounted at a height, at which it is possible to read the linear scale both in the highest position and in the lowest transfer position of the specimen carrier magazines. At the same time it is also necessary to consider a tolerance range for adapting to different heights of the coupling to a microscope stage. In order to be able to keep this tolerance range and with it the height of the magazine carrier frame and the length of the linear scale as small as possible, it is advantageous to insert the magazine carrier frame with its vertical frame members into a stand at different discrete heights that provide the necessary tolerance range for the height adjustment of the coupling frame. The insertion into a stand is advantageous especially for bridging greater height differences, as in the case of tripods of inverted microscopes.

A known system for removing the specimen carriers from the compartments of a specimen carrier magazine provides a gripper, which elastically pushes the specimen carriers against a pressure plate for removal and for transport. In order to deposit in a compartment when the specimen carrier is moved back, this specimen carrier has to be removed from the pressure plate. To this end, a liftable traverse comprising pins that point vertically upwards can be disposed in the coupling frame parallel to the bridge. The pins are dimensioned and positioned in such a way that they can be moved up into the gripper behind a specimen carrier; and, as the gripper is refracted, the pins can remove the specimen carrier from the pressure plate, so that the specimen carrier stays in the compartment.

A manually movable specimen carrier carriage can be mounted preferably on the coupling frame parallel to the bridge. If the magazine lift is moved high enough, the specimen carrier carriage can be pushed under the specimen carrier magazines into a suitable transfer position for the specimen carriers located therein. The height of the loading plane for the specimen carriers into the specimen carrier carriage is adapted to the reference plane formed by the coupling frame in such a way that it coincides with the transfer plane adjusted for a specimen carrier magazine.

An additional advantageous embodiment of the device consists of arranging a frame projection, which extends over the specimen carrier magazines, on the magazine carrier frame. Rollers, pointing towards the open compartments of the specimen carrier magazines, are mounted on the resilient lever arms. The lever arms are tilted towards the specimen carriers, which possibly protrude from the compartments of the specimen carrier magazines in such a way that when the magazine lift moves up and down, the specimen carriers are pushed uniformly into the compartments. This arrangement guarantees that repeatable gripping positions are provided for a handling system for removal of the specimen carriers.

In order to compensate for the weight of the coupling frame and the additional add-on components, it may be advantageous to arrange also a prestressed rewind spring band, the free end of which is fastened to the coupling frame, on the frame projection. As a result, a tilting of the coupling frame and/or jamming of the guide elements of the coupling frame on the bars in the magazine carrier frame is and/or are counteracted.

Other objects, advantages and novel features of the present invention will become apparent from the following detailed description of one or more preferred embodiments when considered in conjunction with the accompanying drawings.

BRIEF DESCRIPTION OF THE DRAWINGS

The drawings show in schematic form one exemplary embodiment of the inventive device, which is described in detail below with reference to the drawings.

DETAILED DESCRIPTION OF THE DRAWINGS

Figure 1:
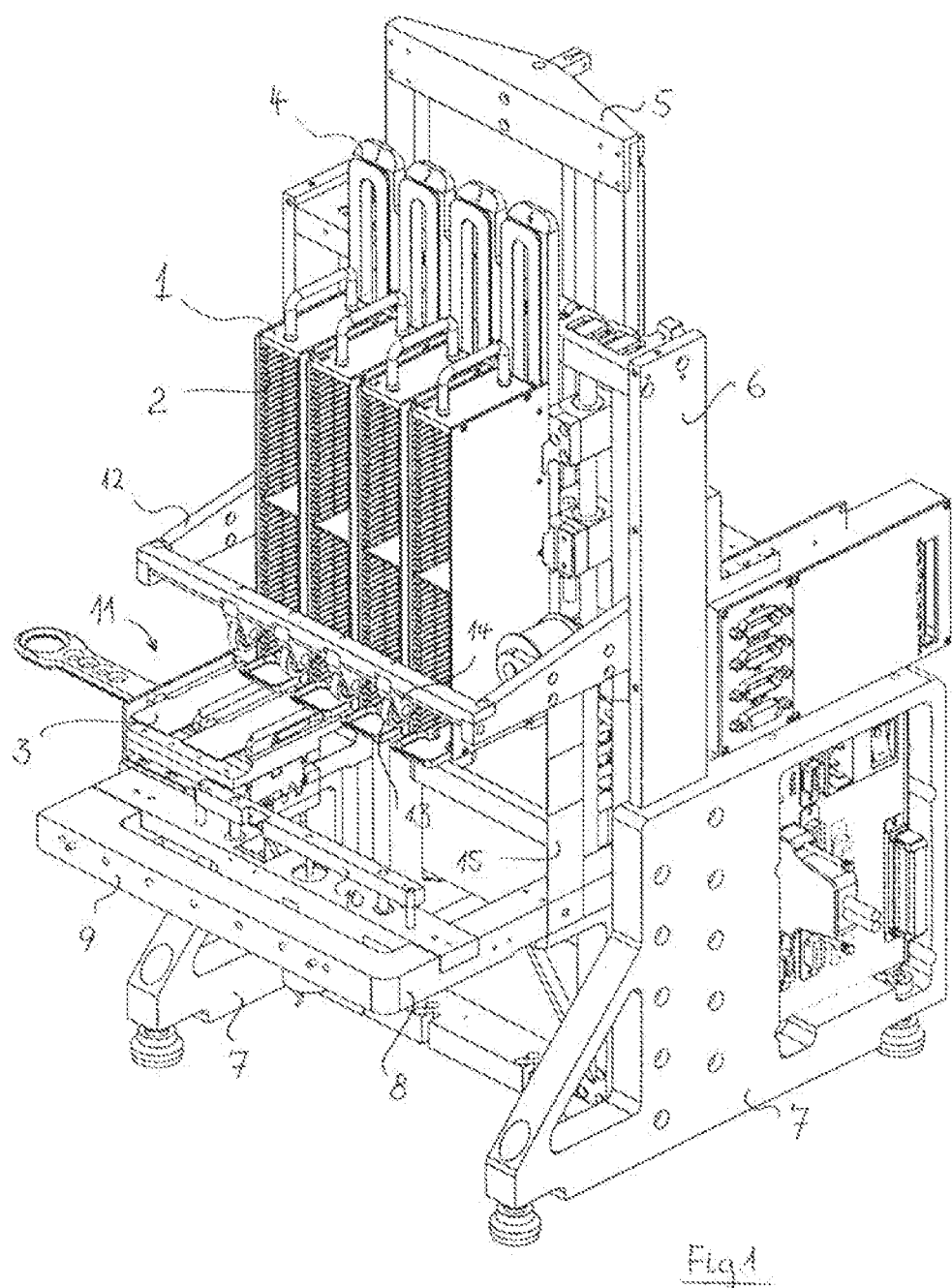
FIG. 1 shows an oblique view of the front side of the device.

The front side, depicted in FIG. 1, shows four specimen carrier magazines 1 with compartments 2 for supplying the specimen carriers 3 that are not shown in this embodiment. The specimen carrier magazines 1 are inserted interchangeably into the rails 4 on a magazine lift 5. The compartments 2 are open on the front side for loading or removal of the specimen carriers.

The magazine lift 5 is mounted in a magazine carrier frame 6 in such a way that it is adjustable for height. The magazine carrier frame 6 is inserted with its vertical frame members into a stand 7. The stand 7 has attachment points at different heights on the vertical frame members. The specimen carriers 3 can be made available for transfer to a microscope stage (not illustrated) by moving the magazine lift 5 in the magazine carrier frame 6.

An equal-sided coupling frame 8 with a bridge 9 is also mounted in a sliding manner in the magazine carrier frame 6. The bridge 9 is provided for making a secure connection with the examination stage of a microscope that is not shown. A traverse 10 that can be raised is inserted into the coupling frame 8 parallel to the bridge 9. The traverse 10 has upright pins, which are not shown in detail. When a specimen carrier 3 is pushed into a compartment 2, these pins can remove the specimen carrier from an automatic gripping device.

A specimen carrier carriage 11, which can be moved by hand in parallel to the bridge 9, is mounted on the coupling frame 8. The specimen carrier carriage 11 has two compartments for receiving the specimen carriers 3. The front ends of the specimen carriers 3 protrude freely from the compartments, so that they can be grasped by an automatic gripping device (not illustrated) for removal and for returning. The height of the compartment plane of the specimen carrier carriage 11 with respect to the reference plane formed by the coupling frame 8 is adapted to the preadjusted transfer plane of the specimen carrier magazines 2 relative to the microscope stage.

A frame projection 12, which extends over the specimen carrier magazines 1, is fastened to the magazine carrier frame 6. Rollers 13 are hinged in a pivotable manner to this frame projection by way of elastically mounted lever arms 14. The rollers 13 are directed towards the open compartments 2 of the specimen carrier magazines 1 and push the specimen carriers 3, which protrude from the compartments 2, as far as to a uniform depth into the compartment 3 when the magazine lift 5 is moved up and down.

The frame projection 12 also serves to fasten a prestressed rewind spring band 15, which is fastened with its free end to the coupling frame 8 and has the effect of reducing the weight of the coupling frame 8 by means of the spring bias, so that when the bridge 9 is screwed to a microscope stage, no one-sided load moments can act on said stage.

Figure 2:
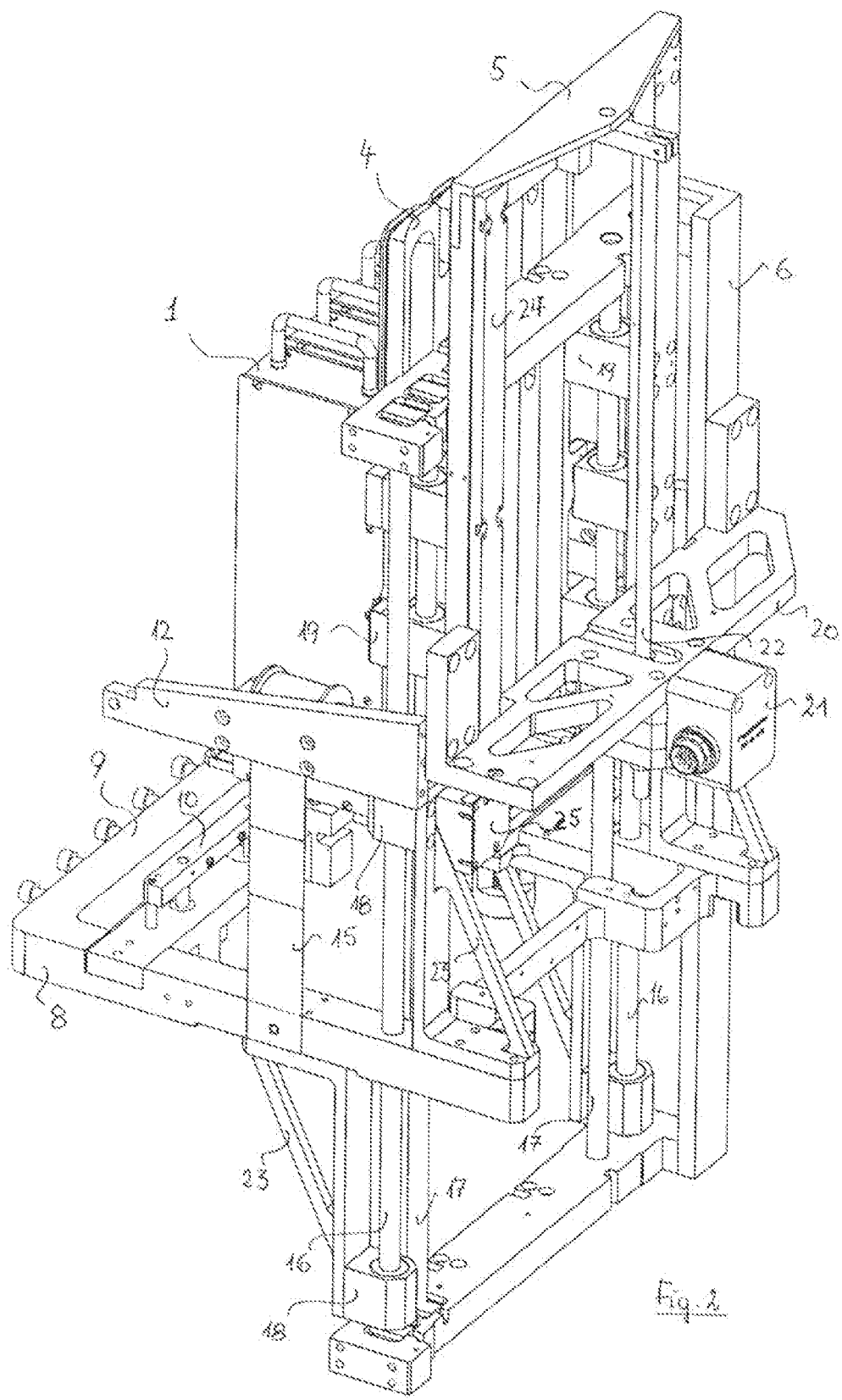
FIG. 2 shows an oblique view of the rear side of the device.

In the rear view of the device shown in FIG. 2, the vertical frame member (located up front in the figure) of the magazine carrier frame 6 is omitted, in order to show more clearly the arrangement of the guide elements for the device parts that move up and down in the magazine carrier frame 6. In order to guide the coupling frame 8 and the magazine lift 5 in the vertical direction, two first and second bars 16, 17 are arranged parallel to each other and to the vertical frame member in close proximity of the vertical frame members of the magazine carrier frame 6. The bars 16, 17 are constructed as round bars. However, bar elements with guide profiles can also be provided.

The magazine lift 5 can be adjusted in height on the first bar 17. The front-sided rails 4 of the magazine lift 5 and the rear-sided magazine lift frame are connected to each other by way of first sliding bushings 19, which run on the first bars 17. A carrier element 20 is fastened to the vertical frame members of the magazine carrier frame 6 transversely to the directions of the bars. A linear motor 21 with a spindle 22 is mounted on said carrier element. The head of the spindle 22 is mounted rotatably in a fixed manner on the upper cross frame of the magazine lift 5, so that when the spindle 22 rotates, the magazine lift 5 is moved up and down.

The coupling frame 8 is mounted in a sliding manner on the second bars 16. The two sliding bushings 18 that surround the two bars 16 are fastened to the coupling frame 8 by way of support brackets 23 and guarantee over their distance a tilt resistant guide of the coupling frame 8 in the magazine carrier frame 6. As a result, the weight relief by means of the rewind spring band 15 prevents the sliding bushings 18 from jamming.

A linear scale 24 is fastened to one of the rear-sided vertical frame members of the magazine lift 5; and assigned to this linear scale is a sensor 25 that is fastened to the coupling frame 8. In the event of a change in the height adjustment of the coupling frame 8, the sensor 25 moves relative to the linear scale 24. The displacement distance determined by the sensor 25 is transmitted to the control unit of the linear motor 21, which moves the linear scale 24 with the magazine lift 5 by way of a suitable control of the spindle 22 in order to compensate for the displacement distance.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A specimen carrier supply and delivery device comprising:
   at least one specimen carrier magazine having separate compartments for receiving interchangeably specimen carriers;
   a magazine lift, which is adjustable in height in a magazine carrier frame for receiving interchangeably specimen carrier magazines,
   two pairs of bars, which stand vertically and parallel to one another, and are arranged in the magazine carrier frame, wherein the magazine lift is guided in a height adjustable manner on two complementary first bars of the pairs of bars;
   an equal-sided coupling frame, which is aligned vertically to the plane formed by the first bars with a bridge, which is arranged parallel to the plane, wherein the equal-sided coupling frame is mounted in a sliding manner on two complementary second bars of the pairs of bars;
   a linear scale, which is aligned parallel to the direction of the bars, and is fastened to the magazine lift;
   a sensor for reading the position of the coupling frame relative to the linear scale, wherein the sensor is disposed on the sliding mounting of the coupling frame; and
   a carrier element, which is aligned transversely to the direction of the bars and is configured for a linear motor with a spindle for adjusting the height of the magazine lift relative to the current position of the sensor, wherein the carrier element is arranged on the magazine carrier frame.

2. The specimen carrier supply and delivery device as claimed in claim 1, wherein the magazine carrier frame with its vertical frame members can be inserted into a stand at different heights.

3. The specimen carrier supply and delivery device as claimed in claim 1, wherein a liftable traverse comprising pins that stand vertically upright is disposed parallel to the bridge inside the coupling frame, which is mounted in a sliding manner.

4. The specimen carrier supply and delivery device as claimed in claim 1, wherein a specimen carrier carriage, which is movable by hand parallel to the bridge, is mounted on the coupling frame.

5. The specimen carrier supply and delivery device as claimed in claim 1, wherein the magazine carrier frame has a frame projection, which extends over the specimen carrier magazines and on which rollers, pointing towards the open compartments of the specimen carrier magazines, are mounted on resilient lever arms.

6. The specimen carrier supply and delivery device as claimed in claim 5, wherein the frame projection has a pre-stressed rewind spring band, the free end of which is fastened to the coupling frame in order to reduce the weight.

* * * * *